(12) United States Patent
Stafford et al.

(10) Patent No.: US 11,124,847 B1
(45) Date of Patent: Sep. 21, 2021

(54) SYSTEMS AND METHODS FOR ASSESSING PERTURBATIONS IN CELLULAR DIFFERENTIATION USING REPORTER CELL LINES

(71) Applicant: Nzumbe, Inc., Portland, OR (US)

(72) Inventors: James M. Stafford, Colchester, VT (US); Michael R. Rountree, Portland, OR (US)

(73) Assignee: NZUMBE, INC., Portland, OR (US)

( * ) Notice: Subject to any disclaimer, the term of this patent is extended or adjusted under 35 U.S.C. 154(b) by 201 days.

(21) Appl. No.: 16/151,204

(22) Filed: Oct. 3, 2018

Related U.S. Application Data

(60) Provisional application No. 62/567,722, filed on Oct. 3, 2017.

(51) Int. Cl.
| | | |
|---|---|---|
| *C12Q 1/68* | (2018.01) | |
| *C12Q 1/6897* | (2018.01) | |
| *C12N 5/074* | (2010.01) | |
| *C12N 15/85* | (2006.01) | |
| *C12N 15/113* | (2010.01) | |
| *C12N 15/52* | (2006.01) | |
| *C12N 15/62* | (2006.01) | |
| *C12N 15/65* | (2006.01) | |
| *C12N 15/67* | (2006.01) | |
| *C12Q 1/02* | (2006.01) | |
| *C12N 5/071* | (2010.01) | |

(52) U.S. Cl.
CPC ......... *C12Q 1/6897* (2013.01); *C12N 5/0696* (2013.01); *C12N 5/0697* (2013.01); *C12N 15/113* (2013.01); *C12N 15/52* (2013.01); *C12N 15/625* (2013.01); *C12N 15/65* (2013.01); *C12N 15/67* (2013.01); *C12N 15/85* (2013.01); *C12Q 1/025* (2013.01); *C07K 2319/02* (2013.01); *C07K 2319/036* (2013.01); *C12N 2015/859* (2013.01); *C12N 2506/03* (2013.01); *C12N 2506/08* (2013.01); *C12N 2510/00* (2013.01)

(58) Field of Classification Search
CPC .... C12Q 1/6897; C12Q 1/025; C12N 5/0697; C12N 15/113; C12N 15/52; C12N 15/625; C12N 5/0696; C12N 15/65; C12N 15/67; C12N 15/85; C12N 2015/859; C12N 2506/03; C12N 2506/08; C12N 2510/00; C07K 2319/02; C07K 2319/036

See application file for complete search history.

(56) References Cited

U.S. PATENT DOCUMENTS

2011/0059439 A1* 3/2011 Bhaumik ............. C12Q 1/6897
435/6.14

OTHER PUBLICATIONS

McNutt et al (Chapter 12 "Cell-Based Assays for Neurotoxins", especially p. 262). (Year: 2015).*
Wilson et al in "Development and differentiation of neural rosettes derived from human embryonic stem cells" (2006: Stem Cell Reviews vol. 2, No. 1: pp. 67-77). (Year: 2006).*
Slotkin et al (Toxicology 2016, Nov. 30, 2016; vol. 372: pp. 42-51). (Year: 2016).*
Malchenko et al (Gene, Jan. 25, 2014: vol. 534, No. 2, pp. 400-407, ePub Aug. 15, 2013). (Year: 2013).*
Hendrickson et al (PLOS ONE published Apr. 7, 2011.) (Year: 2011).*
Couillard et al "Human in vitro reporter model of neuronal development and early differentiation process" (BMC Neuroscience, 2008 vol. 9, pp. 1-9). (Year: 2008).*
Liu et al (Genesis, 2007 vol. 45, No. 9 pp. 1-18). (Year: 2007).*

* cited by examiner

*Primary Examiner* — Catherine S Hibbert
(74) *Attorney, Agent, or Firm* — Alleman Hall Creasman & Tuttle LLP

(57) ABSTRACT

A method for generating a reporter cell line comprises culturing a cell line capable of undergoing two or more consecutive stages of differentiation and performing the targeted insertion of two or more secretable reporter genes into the genome of the cultured cell line to form edited cells. One or more first stage inserted secretable reporter genes are placed under control of promoters for genes canonically expressed during the first stage of differentiation, and one or more second stage inserted secretable reporter genes are placed under control of promoters for genes canonically expressed during the second stage of differentiation but not during the first stage of differentiation. Differentiation of the clonally expanded edited cells is then induced to the first stage of differentiation, thus inducing expression of the first stage inserted secretable reporter genes.

7 Claims, 7 Drawing Sheets

SYSTEMS AND METHODS FOR ASSESSING PERTURBATIONS IN CELLULAR DIFFERENTIATION USING REPORTER CELL LINES

BACKGROUND

Exposure to chemicals and environmental toxins during early development may adversely impact cellular differentiation and organ development. Even subtle shifts in neural differentiation may lead to developmental and cognitive delays, neurological impairments, disease, etc.

SUMMARY

Figure 1:
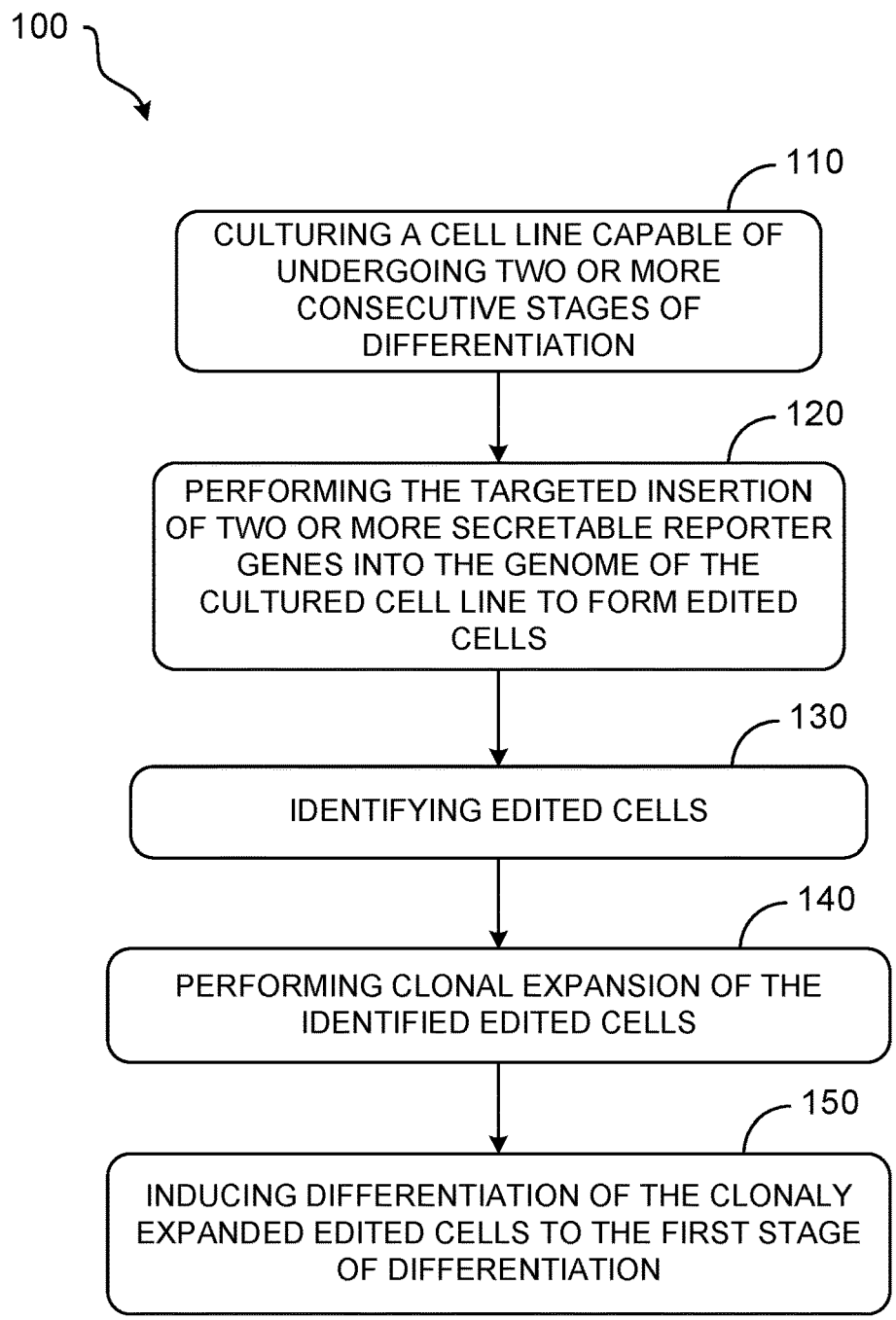
FIG. 1 shows an example method for generating a reporter cell line.

A method for generating a reporter cell line comprises culturing a cell line capable of undergoing two or more consecutive stages of differentiation and performing the targeted insertion of two or more secretable reporter genes into the genome of the cultured cell line to form edited cells. One or more first stage inserted secretable reporter genes are placed under control of promoters for genes canonically expressed during the first stage of differentiation, and one or more second stage inserted secretable reporter genes are placed under control of promoters for genes canonically expressed during the second stage of differentiation but not during the first stage of differentiation. Differentiation of the clonally expanded edited cells is then induced to the first stage of differentiation, thus inducing expression of the first stage inserted secretable reporter genes.

DETAILED DESCRIPTION

Cellular differentiation is an intricate process that depends on tight genetic regulation to proceed as designed. Exposure to environmental toxins during development is known to interfere with differentiation and developmental processes. For example, the developmental origins of health and disease hypothesis predicts that early life exposures contribute to increased risk of disease later in life, presumably via changes in gene expression that interfere with differentiation processes.

Thus, an ongoing problem for human health is that the toxic effects for many, and perhaps most, synthetic chemicals currently in the environment is unknown. Current screening methods that test chemicals for toxic effects are limited, particularly with regard to tests that may provide information that is directly relevant to neurodevelopmental processes in human cells.

During brain development, immature cell types actively differentiate into complex cell types to form neural circuits. This developmental period is thus a time in which cells are highly vulnerable to chemical exposures which may interfere with the inherent regulation of cell differentiation. A major reason for this vulnerability is that neuronal differentiation depends on carefully orchestrated changes in gene expression that can be perturbed by environmental exposures.

This suggests that even subtle perturbations occurring early in brain development may increase later onset risks of neurological impairment and disease. Subtle yet stable changes in gene expression resulting from chemical exposures during early brain development are thus predicted to have life-long consequences. For example, exposure of the prenatal brain to chemical agents such as domoic acid, valproic acid, and methylazoxymethanol, among others, has been shown to induce various cognitive impairments, epilepsies, and neuropsychiatric diseases, depending on the timing and nature of the exposure.

Despite the knowledge of these risk factors, relatively few chemicals present within the environment have been identified which may adversely affect human neural development. Indeed, many chemicals present in the environment have not been screened for neurotoxic effects including activity that interferes with the prolonged and finely tuned neuronal differentiation process.

For example, it is estimated that the ~1,500 compounds tested annually by the Environmental Protection Agency (EPA) represents only 10% of the total compounds tested by industry. For all of these compounds, only basic toxicity testing is done, which fails to capture the complexity of effects on the developing nervous system. Thus, an ongoing problem for human health is a lack of understanding of the toxic effects for most synthetic chemicals. In part, this is due to a lack of methodologies and reagents that may both identify these neurotoxins as well as define how they impact the development of neuronal progenitors, glia, and neurons themselves.

In particular, in vitro neuronal differentiation (e.g., development of a neural progenitor to mature neuronal and/or glial cells) depends on precise timing and technical care over many months. As a result, studying the effect of chemicals on neurodevelopment is cumbersome, utilizes expensive reagents, and takes orders of magnitude longer than traditional chemical screening approaches. Further complicating such research is an intricate balance between neuronal cell types that makes it difficult to discern the most biologically relevant endpoints. The net result is a huge unmet need for reproducible assays that can identify and characterize the effects of chemicals on neural development from the perspectives of both environmental toxicology and drug development.

In an example, this disclosure describes the use of secretable reporter enzymes to measure cell type proportions during differentiation, providing an indicator of the toxic effects of applied perturbation agents. The use of these reporters allows for quantifying markers of differentiation at multiple time points during differentiation without disturbing the cells by merely repeatedly sampling the media from the same culture well.

As an example, a platform is described herein that addresses these challenges within the growing neuro-toxicology market. Such screening platforms may include methods to rapidly and affordably screen factors for their ability to affect human neural differentiation. Such factors may include, but are not limited to chemicals, drugs, environmental toxins/pollutants, small molecules, small RNAs, and genetic alterations. An example screening method includes a reporter-based assay that yields simple, easy to interpret metrics as to how a given chemical affects neurodifferentiation. Such screening assays greatly reduce the time and costs of experimentation. By developing differentiation signatures based on this platform, the disclosed methods yield a short-term assay that provides information predictive of long-term consequence.

FIG. 1 shows an example method 100 for generating a reporter cell line usable for determining the effects of one or more perturbing factors on cellular differentiation. The cell lines generated via method 100 utilize a combination of features to overcome the above described challenges in screening environmental toxins and other factors. In particular, method 100 will be described with regard generating cell lines usable to screen for factors that affect neural differentiation.

At 110, method 100 includes culturing a cell line capable of undergoing two or more consecutive stages of differentiation. Such cell lines may thus be multipotent, pluripotent, omnipotent, or other cell lines capable of differentiating into different cell types by initially differentiating into a first cell type, and then differentiating into one or more second cell types. Such cell types may include embryonic stem cells, fetal stem cells, progenitor cells, induced stem cells, adult stem cells, amniotic stem cells, etc., as well as partially differentiated cells derived from such stem cells which retain the capability of undergoing two or more consecutive stages of differentiation. As an example, the cell line may include human induced pluripotent stem cells (iPS). iPS may be advantageous when compared to other stem cell types, such as embryonic stem cells, in that they can be derived directly from a living, healthy individual as well as from patients harboring a disease. This leaves them unencumbered by many of the regulatory restrictions on using embryonic stem cells. Further, the use of iPS derived from a diseased patient may enable studies as to whether the genetic background of that disease confers a vulnerability to a given neurotoxin. Because of the inherent differences of male and female cells, including sex-based predispositions to certain neurodevelopmental diseases (e.g., Fragile X, Autism Spectrum Disorder, Rett Syndrome), both male and female versions of the iPS cells may be processed via method 100 in parallel.

At 120, method 100 includes performing the targeted insertion of two or more secretable reporter genes into the genome of the cultured cell line to form edited cells. For example, the two or more secretable reporter genes may include one or more first stage inserted secretable reporter genes placed under control of promoters for genes canonically expressed during a first stage of differentiation, and one or more second stage inserted secretable reporter genes placed under control of promoters for genes canonically expressed during a second stage of differentiation, but not during the first stage of differentiation. As an example, secretable reporter genes may be inserted into the endogenous loci of genes known to be expressed in one (and only one) of the major types of cells present during neural differentiation. These may include very early stage human neural rosettes, human neuronal progenitor cells (hNPCs), various subclasses of neurons (e.g. pyramidal cells, inhibitory interneurons, purkinje cells), oligodendrocytes, and astrocytes. In one example, reporter genes are inserted into one gene associated with each cell type. In such an example, each main cell type will express one reporter gene. However, in some examples, two or more markers for one or more of the main cell types may be inserted into the initial cultured cells.

Although described primarily with regard to neuronal cell types, method 100 may also be applied to other cell types capable of undergoing two or more consecutive stages of differentiation. This may include cells such as microglia that are critical for the functioning of the nervous system by share features of myeloid origin. In this and other examples, two or more secretable reporter genes may be inserted into the genome of hematopoietic stem cells, cardiomyocytes, or other cells that undergo two or more stages of differentiation. First stage inserted secretable reporter genes may be placed under control of promoters for genes canonically expressed by common lymphoid progenitor cells in the case of a hematopoietic system, or early mesodermal or cardiac progenitors. Second stage inserted secretable reporter genes may be placed under control of promoters for genes canonically expressed by B Cells, NK cells, T Cells, and myeloid cells (e.g., microglia, macrophages) in the hematopoietic lineage, and cardiac precursors and/or mature cardiomyocytes in the cardiac lineage.

Figure 2:
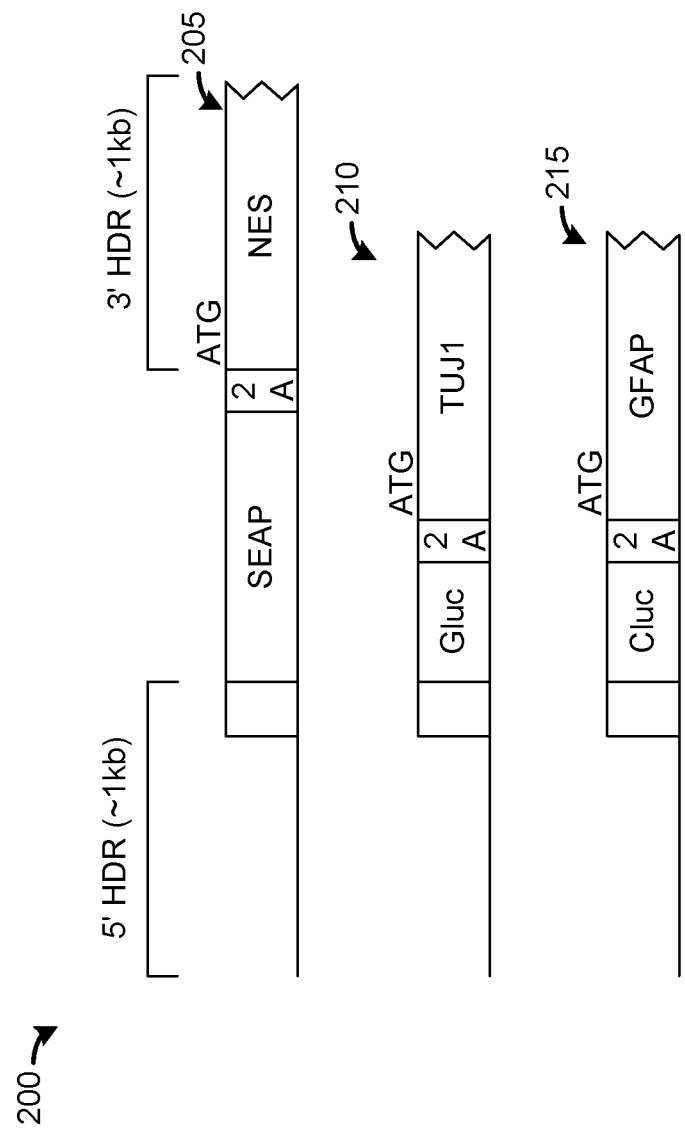
FIG. 2 shows an example set of gene constructs.

FIG. 2 shows example set of gene constructs that may be utilized in method 100. At 200, three genes associated with neural differentiation are shown. Nestin (NES) (205) is a gene specifically expressed by hNPCs. Neuron-specific class iii beta-tubulin (TUJ1) (210) is a gene specifically expressed by neurons, and glial fibrillary acidic protein (GFAP) (215) is a gene specifically expressed by glia. However, additional or alternative genes may be used as markers for each cell type that reflect the diversity of the developing nervous systems and specific application of the assay.

The basic components of the targeting constructs include reporter genes (SEAP, Gluc, Cluc), a self-cleaving P2A peptide sequence, and 5' and 3' flanking homology directed regions (HDRs) of target genes (NES, TUJ1, GFAP). As depicted, each reporter gene has been inserted between the marker gene and the promoter region for the marker gene. In this example, secreted embryonic alkaline phosphatase (SEAP) has been inserted alongside NES, Gaussia luciferase (GLuc) has been inserted alongside TUJ1, and Cyprindia Luciferase (CLuc) has been inserted alongside GFAP. In some examples, the combinations of reporter genes and marker genes may be altered.

The reporter genes may be fused in-frame via the P2A peptide sequence to the start codon of the target gene, and/or to the 3' end of the target gene. The P2A element encodes a short peptide (~20 aa) that, when fused in-frame between ORFs of multiple genes, produces equimolar levels of multiple proteins translated from the same mRNA. Thus, when targeted, the ORF of both the reporter gene and the endogenous gene will be transcribed from the target gene's promoter and will respond to neural differentiation signals appropriately.

This configuration may permit uninterrupted expression and creation of the target gene's protein product. Cleavage of the secretable enzymes from the structural proteins encoded by NES, TUJ1, and GFAP occurs during translation, prior to incorporation of the structural protein in the cell's cytoskeletal, thus not affecting protein function. Other self-cleaving peptides may be incorporated into the reporter gene constructs in addition to or as an alternative to P2A. For example, other 2A family elements, such as T2A, E2A, and F2A may be used. Alternatively, internal ribosome entry sites (IRES) may be included. In some examples, the reporter gene may be inserted directly into one of the alleles of a target gene, provided that knocking out one allele of the gene is not otherwise detrimental to growth and differentiation of the cells.

Each of the indicated reporter genes encode enzymes that are secreted out of the cell into the culture medium. By utilizing secretable enzymes as reporters, the differentiation of the hNPCs may be ascertained at numerous time points throughout the differentiation process with minimal perturbation to the cells. Other secretable enzymes may be used as reporters, including, but not limited to, *Gaussia*-Dura Luciferase, Oplophorus Luciferase (Oluc), Metridia luciferase (mLuc), Secretable fluorescent proteins (GFP, RFP, etc.), and/or any quantifiable enzyme that can be engineered via the addition of a secretory signal.

Although in this example, the reporter genes are targeted for insertion at the site of a known marker gene, in some examples, neurodevelopmental-specific promoters may be used to drive reporter gene expression at other integration sites. The engineered reporter gene plasmids may be allowed to integrate either randomly into the genome or to a specified locations (e.g. a safe harbor locus). In this way, the expression of the marker gene may be unperturbed, allowing for more endogenous expression of the marker genes, and thus a more representative picture of differentiation.

In further examples, the secretable reporter genes may be inserted in conjunction with an additional reporter gene (e.g. antibiotic resistance gene or fluorescent protein gene). Such an additional reporter could aid in the genome editing and/or other downstream applications. In some examples, the first stage secretable reporter genes may be inserted into genes that are not expressed, or show a decreased expression at the second stage, thereby the first stage reporter may be down-regulated upon differentiation to the second stage of differentiation.

In some examples, additional genomic editing and/or perturbation may be performed on the edited hNPCs prior to proceeding to neural differentiation stages. For example, a CRISPR-KO screen, shRNA screen, and/or other genetic manipulation may be performed, thus generating libraries of hNPCs having one or more genes knocked out. Targeted, random, or pseudo-random mutations may be made within the hNPCs to assess the effect of such mutations on neural differentiation. In some examples, neurological disease-causing mutations and/or associated genetic mutations may be generated, such as in the HTT gene, known to cause Huntington's Disease, the NOTCH3 gene, known to cause Cerebral Autosomal Dominant Ateriopathy with Subcortical Infarcts and Leukoencephalopathy (CADASIL), SCN1A, associated with Dravet Syndrome, MECP2, associated with Rett syndrome, CREBBP, associated with Rubinstein-Taybi Syndrome, etc. Such approaches may allow for the study of diseases where the underlying genomic aberration may have either complete or incomplete penetrance. In this way, drugs and/or other therapeutic agents may be screened to determine whether proper neural differentiation may be restored.

Returning to FIG. 1, at 130 method 100 includes identifying cells that have been edited to include each of the inserted secretable reporter genes. For example, insertion of the secretable reporter genes may be confirmed via PCR screening. Additionally or alternatively, edited cells may be analyzed for reporter gene expression (e.g., via fluorescent microscopy and/or cytometry). In some examples, a selectable marker, such as an antibiotic resistance gene may be expressed from a ubiquitous promoter that could subsequently be deleted (e.g., via flanking lox sites). In some examples, edited cells that are identified to express one or more, but not all of the reporter genes targeted for insertion may be identified as control cells. Multiple rounds of editing and identification may be performed in order to achieve proper integration of all of the inserted secretable reporter genes.

Identification may include producing cultures that are enriched for each of the prospective differentiated cell types. As such, identification may include directed differentiation protocols to enrich for cells differentiated to the first stage, second stage, etc. As a negative control, isogenic cells lacking the reporter genes may be carried through these validation experiments in parallel.

At 140, identified edited cells may be subject to clonal expansion. In this way, cell lines containing the inserted reporter genes may be established. Following clonal expansion, at 150, method 100 may include inducing differentiation of the clonally expanded edited cells to the first stage of differentiation, thus inducing expression of the first stage inserted secretable reporter genes. In many examples, inducing differentiation of the clonally expanded edited cells to the first stage of differentiation will not induce expression of the second stage inserted secretable reporter genes. However, in examples where one or more genetic mutations have been inserted, the expression of one or more of the inserted secretable reporter genes may be altered from their canonical stage.

For example, edited iPS cells with the constructs shown in FIG. 2 may be subject to neural induction, yielding edited hNPCs that express SEAP from the Nestin locus, but do not express Gluc from the TUJ1 locus or Cluc from the GFAP locus. Neural induction of iPS cells may be performed in a suitable culture medium including one or more growth factors and/or other factors that are known to induce differentiation of iPS cells to hNPCs.

Method 100 may thus yield a composition of matter, such as neuronal progenitor cells edited to express one or more inserted secretable reporter genes placed under control of promoters for genes canonically expressed by neuronal progenitor cells, one or more inserted secretable reporter genes placed under control of promoters for genes canonically expressed upon differentiation of the neuronal progenitor cells to neurons, and one or more inserted secretable reporter genes placed under control of promoters for genes canonically expressed upon differentiation of the neuronal progenitor cells to glial cells.

Figure 3:
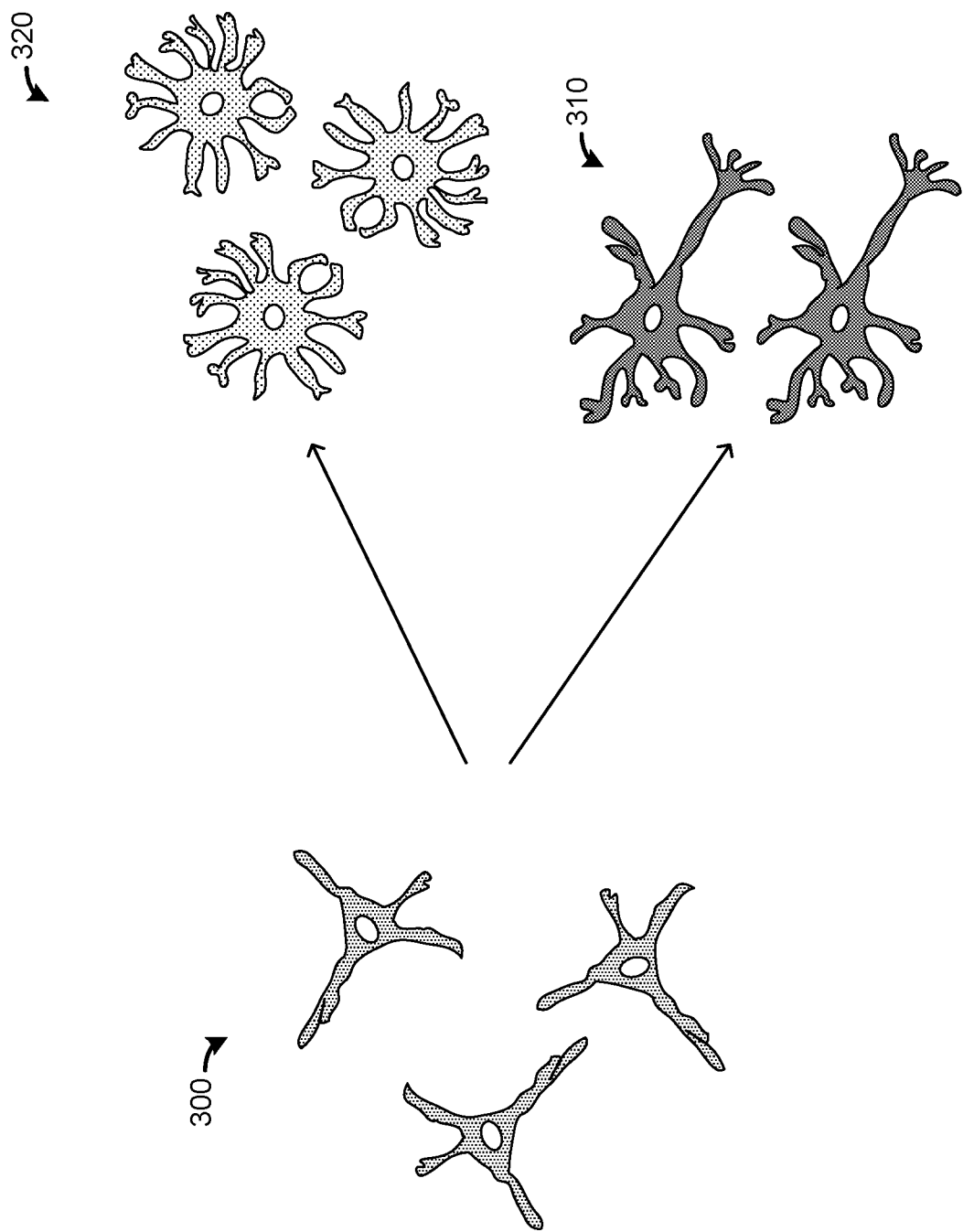
FIG. 3 schematically shows the differentiation of human neural progenitor cells.

FIG. 3 shows an example of such edited human neuronal progenitor cells 300. Cultures of edited hNPCs may be evaluated periodically for differentiation into neurons secreting a first reporter enzyme (shown at 310), glial cells secreting a second reporter enzyme (shown at 320), and undifferentiated neural progenitors expressing a third reporter enzyme. The relative proportion of the three secretable reporters will provide a profile of the balance of hNPCs, neurons, and glial cells present throughout neural differentiation. In some examples, additional downstream markers may be used, such as markers of neurons that give rise to the telencephalon (e.g., PAX6), dorsal (CUX1) and ventral regions (CTIP2) of the cortex, projection neurons (FEZF2), inhibitory interneurons (GAD65/67), and subclasses of these (e.g., PVALB, CCK). As such, edited hNPCs may include markers of third stage, and/or further stages of differentiation that may be evaluated throughout differentiation.

Figure 4:
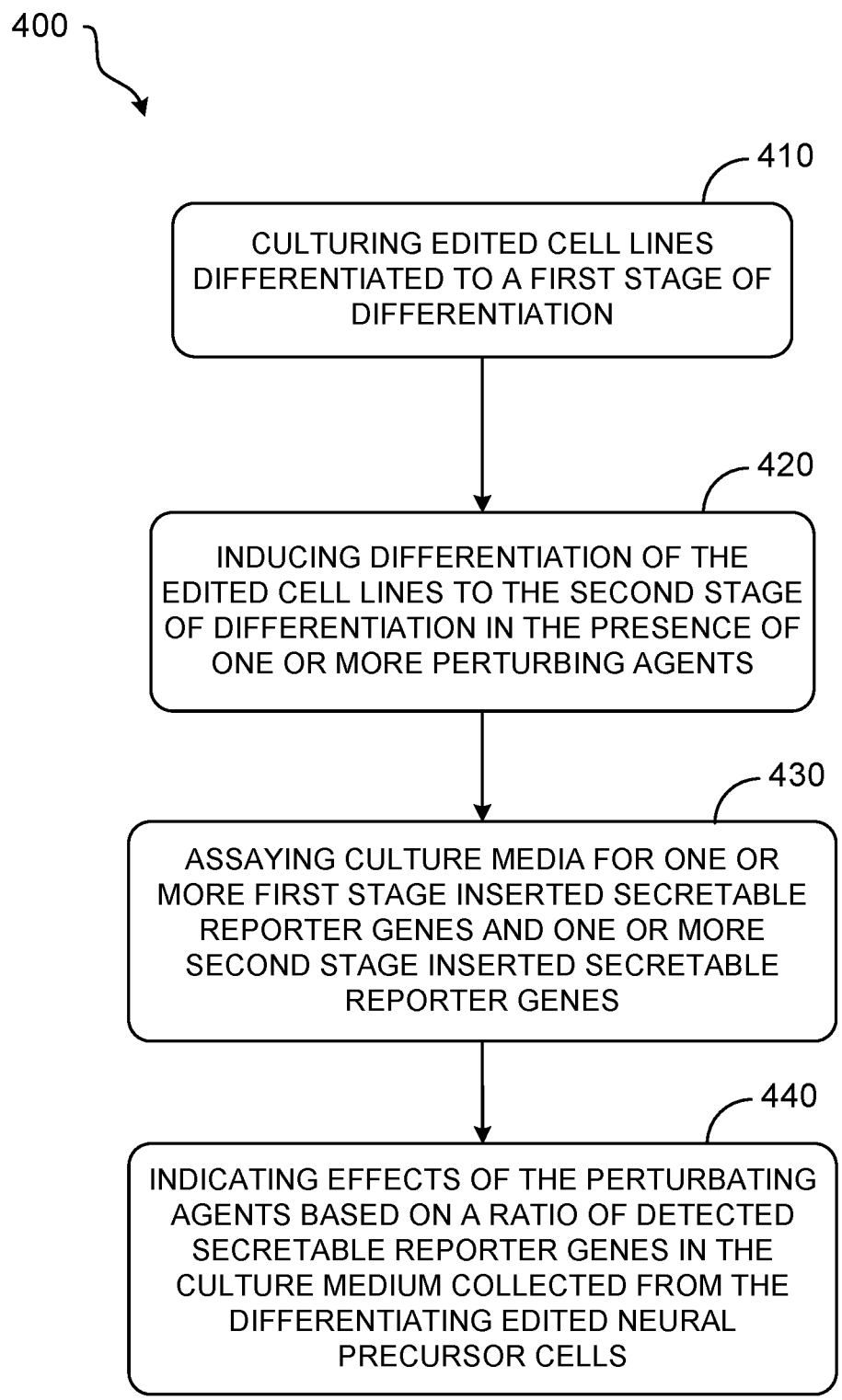
FIG. 4 shows an example method for indicating the effect of a perturbating agent on cellular differentiation.

FIG. 4 shows an example method 400 for indicating the effect of a perturbating agent on cellular differentiation. As one example, method 400 may be used to create and calibrate a screening assay using human iPS-derived hNPCs primed to differentiate into neurons and glial cells. At 410, method 400 includes culturing edited cell lines differentiated to a first stage of differentiation. Such edited cell lines may be edited to express: one or more first stage inserted secretable reporter genes expressed placed under control of promoters for genes canonically expressed during a first stage of differentiation; and one or more second stage inserted secretable reporter genes placed under control of promoters for genes canonically expressed upon differentiation of the edited cells to a second stage of differentiation, but not during the first stage of differentiation. As described with regard to FIG. 3, this may include hNPCs expressing a secretable reporter gene from one or more hNPC specific markers (e.g. NESTIN, SOX2, PAX6, MUSASHI1), and edited to express one or more secretable reporter genes from one or more glial specific markers (e.g., GFAP, MOG, OLIG2) and/or to express one or more secretable reporter genes from one or more neuronal specific markers (e.g., TUJ1, MAP2). Culturing may be performed in medium or high-throughput formats (e.g., 96 well+plates) or in any suitable culturing vessel.

In such examples, method 400 may be applied in order to determine how a toxin affects the dynamic complexities of neurodevelopment. The differentiation process may entail the sequential generation of neurons and the glial cells that support them from a relatively pure hNPC population. The hNPCs may thus be differentiated to a functional and balanced population of cortical neurons and glial cells through the addition of defined culture media supplemented with the requisite trophic factors. Such a human cortical differentiation system offers significant advantages in modeling human neurodevelopment relative to rodent systems because it can detect discrete molecular and functional changes indicative of a host of psychiatric and neurodevelopmental diseases ranging from schizophrenia to epilepsy and profound intellectual disabilities characterized by cortical malformations.

At 420, method 400 includes inducing differentiation of the edited cell lines to the second stage of differentiation in the presence of one or more perturbing agents. For example, edited hNPCs may be cultured in medium containing growth factors and/or other reagents known to induce neural differentiation. The edited hNPCs may be cultured in the presence of one or more chemicals, drugs, environmental toxins/pollutants and/or other factors which may impact on neural differentiation. In some examples, the edited hNPCs may be exposed to the perturbing agents for a duration (e.g., 24 hrs) prior to the induction of differentiation. In other examples, the edited hNPCs may be exposed to the perturbing agents following a predetermined time period after the induction of differentiation. Exposure to the perturbing agents may be for a predetermined time period, a time period based on the identification of one or more factors in the cell culture, throughout differentiation, etc. When two or more perturbing agents are used, the timing of cellular exposure to each agent may be the same, or may be different.

For example, a variety of metals and metal compounds containing nickel, lead or mercury readily cross the placenta and blood-brain barrier, with select populations of pregnant mothers and children being particularly vulnerable to a toxic level of exposure. Such metals are universally neurotoxic, but vary slightly in degrees of the cognitive impairments and neuropathology depending on dose and exposure duration. Heavy metals have also been shown to alter the epigenome of the brain and other exposed tissues with some reports of their toxic effects persisting in a transgenerational manner.

Endocrine disruptors are widespread in the environment and include bisphenol A (BPA), polychlorinated biphenyls (PCBs), and phthalates. All of these chemicals have toxic impacts on the brain with links to potential epigenetics activities in a fairly extensive literature. These activities include disruption of DNA methylation and histone modifications.

Many pesticides, pollutants and naturally occurring compounds have direct deleterious activity on neuronal signaling pathways, and may be considered to be neuroactive compounds. There is growing appreciation for the neurodevelopmental risk and exposure levels to pesticides such as chlorpyrifos and the heavily regulated TCDD (commonly termed dioxin; component of Agent Orange). These compounds act directly on the cholinergic and neuronal aryl hydrocarbon receptor systems, respectively, with links to pathological disease outcomes including those from neurotoxic effects. Naturally occurring compounds such as MAM also have a profound effect on the developing nervous system with defined outcomes in vivo. Another of these, domoic acid similarly produces epilepsy phenotypes and cortical lesions in populations of marine mammals with some reports in humans.

Of great importance in modern neurotoxicology is the growing use of neuropsychiatric therapies during pregnancy and in children where the brain presents significant neurodevelopmental vulnerability. The compound VPA is a histone deacetylase inhibitor used to treat epilepsy and is a bona fide factor for producing autism, neurodevelopmental delay and cognitive impairment in the children of mothers who used VPA during pregnancy. Of growing concern are antidepressants used during pregnancy including both tricyclic and selective serotonin re-uptake inhibitors (S SRI). Mixed epidemiological data as well as recent studies showing their effect on gene expression in human neural stem cells indicate the need for more study in defined systems.

In some examples, the edited hNPCs may be cultured in the presence of one or more shRNA and/or siRNA constructs, thereby knocking down expression of one or more genes. In this way, genes that affect neural differentiation may be rapidly screened for. In some examples, the perturbing agent may be an induced genetic mutation.

At 420, method 400 includes assaying culture media for the one or first stage inserted reporter genes and the one or more second stage inserted reporter genes. For example, cultures of edited hNPCs may be evaluated periodically for differentiation into neurons secreting a first reporter enzyme, glial cells secreting a second reporter enzyme, and undifferentiated neural progenitors expressing a third reporter enzyme.

As an example, for cells grown in standard 96 well plates, each reporter enzyme may be measured in as little as 10 µl of media in a simple benchtop luminometer microplate reader. This allows one to determine the relative proportion of each reporter enzyme by simply assaying a small amount of culture medium (e.g., no requirement for cell lysis). This reporter technology allows the cells to remain healthy while giving a quick and easy-to-interpret metric that assesses whether a putative toxin causes an imbalance in key cell types involved in normal neurodevelopment (e.g., higher or lower expression of each reporter).

By maintaining the cells in culture and assaying the medium, multiple time points may be assessed without perturbing the living cells. In doing so the complexities of a dynamic neural differentiation process may be fully captured while the screening assay remains rapid, affordable and simple to implement.

For example, differentiating hNPCs pass through three significant junctures that aid in gauging the impact of a neurotoxin on the prolonged differentiation process. These stages include the more homogeneous hNPC stage, a heterogeneous intermediate stage (21 days following initiation of differentiation), and a maturing stage that incorporates fully functional neurons and the glial cells that support them (50 days).

At 440, method 400 includes indicating a ratio of detected secretable reporter genes in culture medium collected from the differentiating edited neural progenitor cells. In the hNPC example, the relative proportion of the secretable reporters will provide a profile of the balance of hNPCs, neurons, and glial cells present throughout neural differentiation. Such a ratio may predictive of differentiation in later stages. For example, a threshold ratio determined during the first stage of differentiation may be indicative of changes in expression and/or differentiation at the second stage and/or at later stages. Using such a predictive approach may allow for a decrease in the time and cost associated with traditional screening assays that progress to a later or terminal stage of differentiation before quantifying a result.

Figure 5:
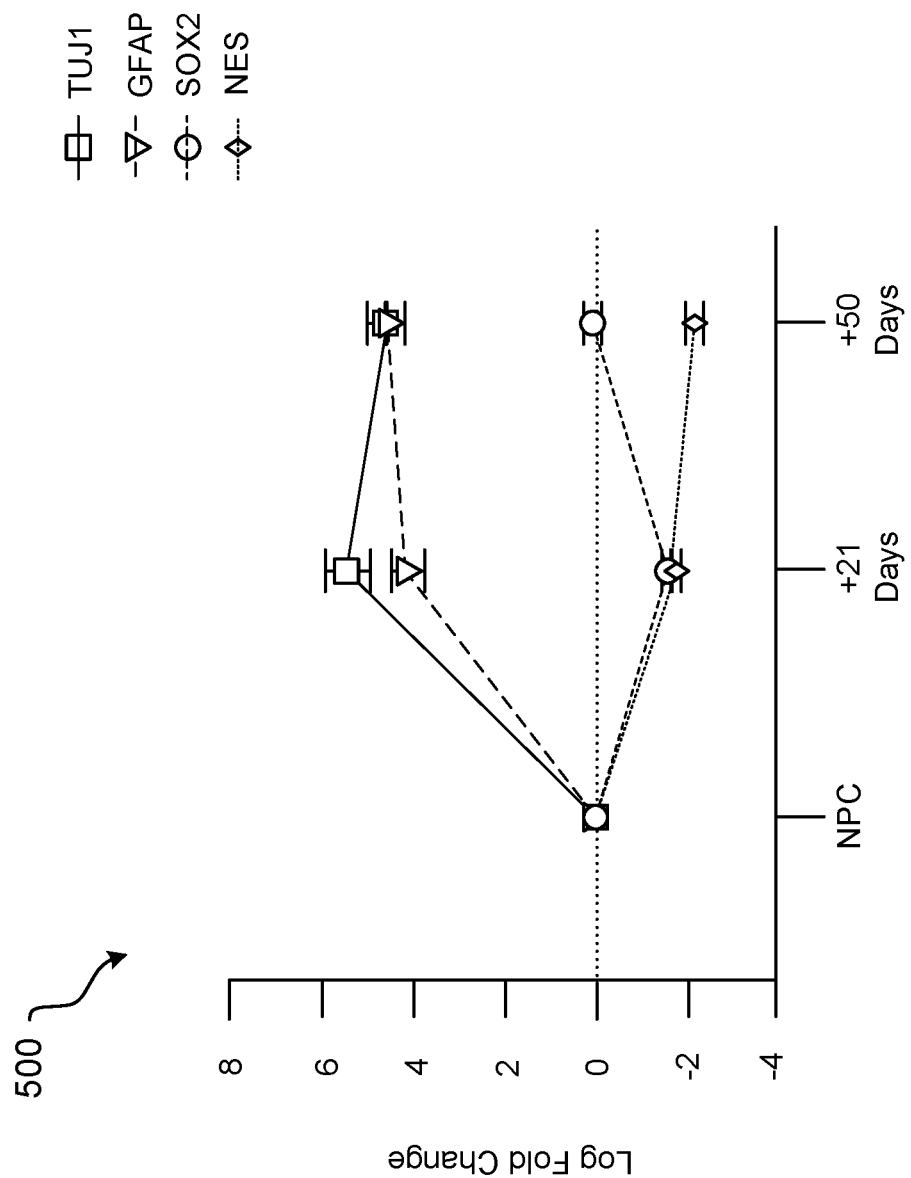
FIG. 5 shows a plot indicating endogenous gene expression during successful neural differentiation.

In an example, high-content cell analysis from cells grown in each well in a 96-well plate was sufficient to detect multiple markers via antibody staining and to be normalized to the DAPI signal, a common baseline measure of DNA content. FIG. 5 shows a plot 500 indicating expression of endogenous genes during successful neural differentiation based on immunofluorescence staining followed by high-content cell analysis. In this example, hNPC are indicated by NESTIN (NES) and SRY-Box 2 (SOX2). Glial Fibrillary Acidic Protein (GFAP) is used as a marker of glial cells (both astrocytes and radial glia), and the neuron-specific class III β-tubulin (TUJ1) is used to indicate neurons. Expression of both GFAP and TUJ1 increased at 21 days and 50 days following differentiation, while both SOX2 and NES decreased at 21 days. Levels of SOX2 expression returned to baseline following 50 days. These results are indicative of the precise changes in cell types achieved during unperturbed differentiation.

In some examples, method 400 may be used to detect immediate changes resulting from neurotoxin exposure, as well as identifying early perturbations that may predict long-term, biologically-relevant changes in the neurodevelopment process.

Figure 6:
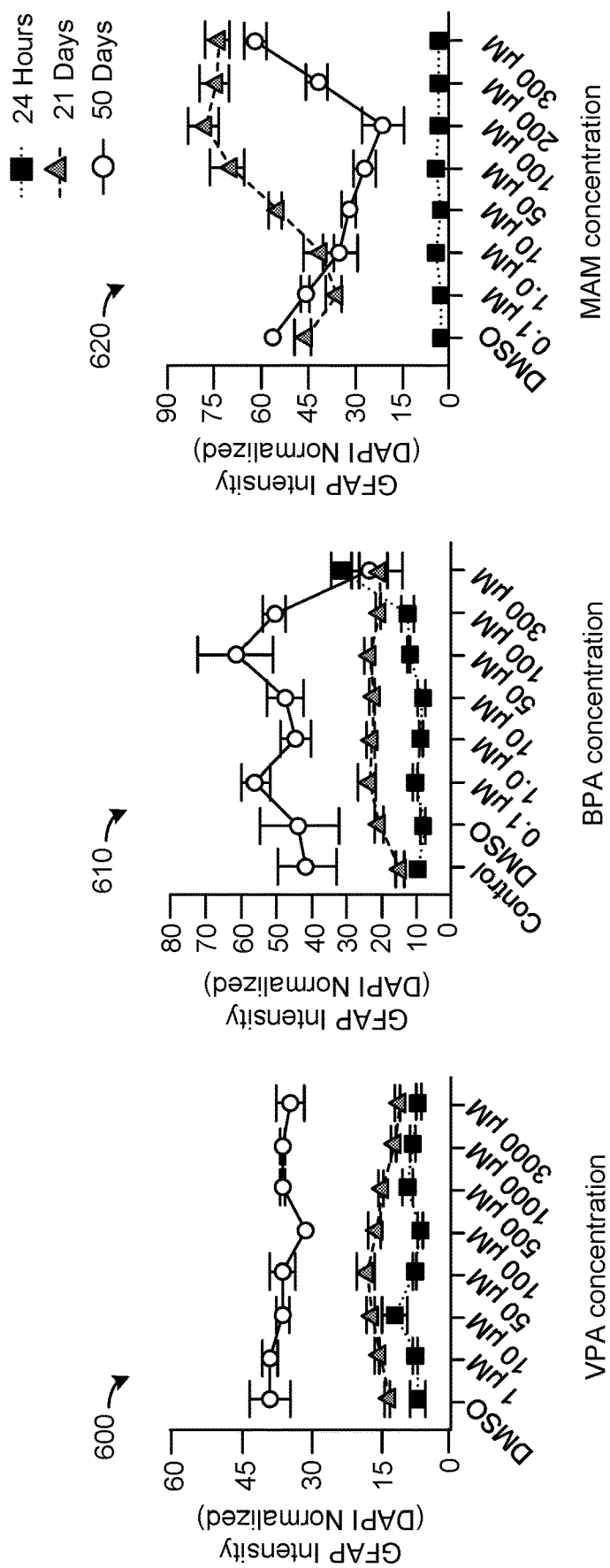
FIG. 6 shows plots indicating the impacts on neuronal differentiation of three neurotoxins.

FIG. 6 shows plots indicating the impacts on neuronal differentiation of three neurotoxins with known epigenetic effects. Plot 600 indicates an experiment using the tox21 chemical valproic acid (VPA), which can cause neuronal deficits when persons are exposed in utero and is known to inhibit histone deacetylation. Plot 610 indicates an experiment using the tox21 chemical bisphenol A (BPA), which interferes with brain development in rodent models and can perturb the epigenome via unknown mechanisms. Plot 620 indicates an experiment with methylazoxymethanol (MAM), the active metabolite and precursor of the Tox21 chemicals 1,2 dimethylhydrazine and formaldehyde, respectively. MAM interferes with complex gene expression pathways, histone modifications, and DNA methylation patterns during brain development, as well as being associated with epilepsy and cortical malformation phenotypes in rodent models.

A broad range of doses for each toxin was selected to determine the dose response and capture the full range to which a developing human brain may be exposed. Cultured hNPC's were treated for 24 hours to avoid complications associated with non-specific toxicity that may occur with chronic treatment, and because we were interested in whether early, acute exposure produces long-term effects detectable in our assay. The glial marker, GFAP, was used to demonstrate basic proof-of-principle.

First, GFAP showed consistent changes under the control condition (DMSO) across differentiation where there is a robust increase from the 24 hour hNPC stage through the 21D and maturing 50D time points. Second, systematic dose-dependent alterations in the level of GFAP were observed for each neurotoxin. Perhaps the most profound was the striking increase in response to increasing doses of MAM at 21D, whereas there was a general decrease at the 50D time point. In contrast, low to moderate doses of BPA produced an increase in GFAP at 21D and 50D time points, with VPA showing more modest effects. These findings provide evidence that method 400 can detect changes in cellular differentiation produced by neurotoxins over time.

In particular, early changes (24 hour and 21D) were identified that predict long-term and disease relevant consequences of a neurotoxin. Additionally, these results begin to elucidate signatures that may facilitate classification of neurotoxins based on their functional effects on discrete neurodevelopmental processes.

Figure 7:
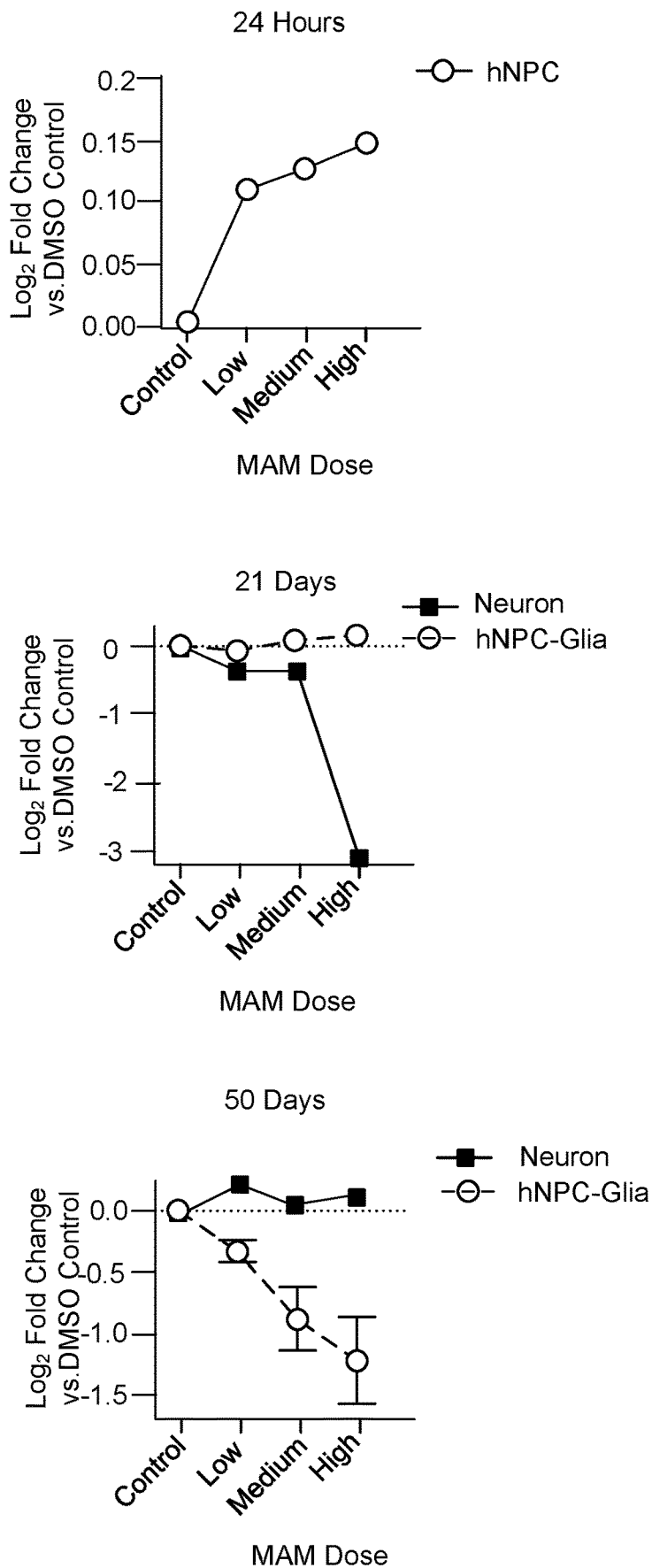
FIG. 7 shows plots indicating the impacts on neuronal differentiation of methylazoxymethanol.

FIG. 7 shows experimental results using MAM as a prototypical neurotoxin that reveal changes that track through the differentiation process. An early change was the clear dose-dependent increase in both hNPC markers (NESTIN and SOX2) at 24 hours (plot 700). Both markers of hNPC as well as glial cells (hNPC-GLIA) showed a similar significant increase across MAM doses at 21 days (plot 710). At 21 Days a significant increase occurred in the hNPC-GLIA population concomitant with a striking decrease in the neuronal population as a function of increasing MAM dose. Remarkably, this trend was reversed at 50 Days (plot 720) where the neuronal population increased and the hNPC-GLIA population decreased, suggesting repopulation of neuronal cells depleting the hNPC. Increases in hNPC-GLIA marks at 21 days and NEURON at 50 days appear subtle due to the relatively large decreases in NEURON at 21 days and hNPC-GLIA at 50 days. However, these differences are significant highlighting the ability of this method to detect both large and small effects produced by neurotoxins. Thus, these results indicate that early events such as the elevated hNPC-GLIA markers are predictive of later changes in the balance of NEURON vs. hNPC-GLIA cell populations during differentiation.

For MAM exposure, these changes may reflect an early proliferation of a hNPC and glial niche that become exhausted at later time points thereby leading to an aberrant level of neuronal populations. Strikingly, an imbalance in this type of niche, referred to as radial glia, is seen in rodent models of cortical malformations and epilepsy and relates to structural changes in brain morphology manifesting in the human diseases themselves (e.g., aberrant cortical layering, altered connectivity).

As such, using the systems and methods described herein, a small group of markers may be used to determine the effect of a perturbing agent (neurotoxin, chemical, biologic, etc) on cellular differentiation. In this way, the balance between surrogate markers of the different cell types may be evaluated to give a readout for the effect of an agent on the differentiation process. The reporter output thus enables the categorization of toxins based on their predicted effects in human disease.

Whereas conventional methods may take months to determine the effect of a toxin on the neural differentiation process, the systems and methods described herein utilize predictive reporter assays that give results in a few days. Perturbations in combinations of these markers can be detected at very early timepoints (hours to days) that are predictive of later, more stable changes in the neural differentiation process. Thus, by using combinations of predictive markers the effect of any given agent on the differentiation process may be rapidly detected, whereas other approaches require weeks to months.

Furthermore, this approach uses a defined neural differentiation approach that includes parameters that make it directly applicable to medium-high throughput screening. This platform is scalable to high-throughput applications (e.g., 96-well+plates) generating a relatively low cost screening platform.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A method for indicating the effect of a perturbating agent on cellular differentiation, comprising:
   culturing edited cell lines differentiated to a first stage of differentiation and edited to express:
     one or more first stage inserted secretable reporter genes placed under control of promoters for genes canonically expressed during a first stage of differentiation; and
     one or more second stage inserted secretable reporter genes placed under control of promoters for genes canonically expressed during a second stage of differentiation, but not during the first stage of differentiation, wherein the one or more second stage inserted reporter genes are different than the one or more first stage inserted reporter genes;
   inducing differentiation of the edited cell lines to the second stage of differentiation in a presence of one or more perturbing agents;
   collecting culture media at one or more time points from the differentiating edited cell lines in the presence of the one or more perturbing agents;
   assaying the collected culture media for the one or more first stage inserted secretable reporter genes and the one or more second stage inserted secretable reporter genes; and
   indicating a ratio of detected one or more first stage inserted secretable reporter genes compared to detected one or more second stage secretable report genes in the collected culture media.

2. The method of claim 1, wherein the edited cell lines comprise edited neuronal progenitor cells.

3. The method of claim 2, wherein the one or more first stage inserted secretable reporter genes are placed under control of a promoter for a gene encoding Nestin.

4. The method of claim 2, wherein inducing differentiation of the edited cell lines to the second stage of differentiation includes inducing differentiation of the edited neuronal progenitor cells to neurons and glial cells.

5. The method of claim 4, wherein the one or more second stage inserted secretable reporter genes are placed under control of promoters for genes encoding TUJ1 and GFAP.

6. The method of claim 1, wherein the edited cell lines comprise one or more targeted genetic mutations inserted into a genome of the edited cell lines.

7. The method of claim 1, wherein the perturbing agent is a neurotoxin.

* * * * *